(12) United States Patent
Xiao et al.

(10) Patent No.: US 7,771,944 B2
(45) Date of Patent: Aug. 10, 2010

(54) METHODS FOR DETERMINING GENETIC HAPLOTYPES AND DNA MAPPING

(75) Inventors: Ming Xiao, Huntingdo Valley, PA (US); Pui-Yan Kwok, San Francisco, CA (US); Paul Selvin, Urbana, IL (US); Mathew Gordon, Palo Alto, CA (US)

(73) Assignees: The Board of Trustees of the University of Illinois, Urbana, IL (US); Regents of the University of California, Oakland, CA (US)

( * ) Notice: Subject to any disclaimer, the term of this patent is extended or adjusted under 35 U.S.C. 154(b) by 0 days.

(21) Appl. No.: 11/957,216

(22) Filed: Dec. 14, 2007

(65) Prior Publication Data

US 2009/0155780 A1 Jun. 18, 2009

(51) Int. Cl.
*C12Q 1/68* (2006.01)
*C12P 19/34* (2006.01)

(52) U.S. Cl. .......................................... 435/6; 435/91.1
(58) Field of Classification Search ........................ None
See application file for complete search history.

(56) References Cited

U.S. PATENT DOCUMENTS 6,607,888 B2 * 8/2003 Schwartz et al. ................ 435/6
2007/0161028 A1 * 7/2007 Schwartz et al. ................ 435/6

FOREIGN PATENT DOCUMENTS

WO WO 02101095 A1 * 12/2002

OTHER PUBLICATIONS

Schwartz et al., "Ordered Restriction Maps of *Saccharomyces cerevisiae* Chromosomes Constructed by Optical Mapping," Science, 1993, vol. 262, pp. 110-114.*
Xiao et al., "Rapid DNA mapping by fluorescent single molecule detection," Nucleic Acids Research, 2007, vol. 35, No. 3, e16, pp. 1-12 [published on-line Dec. 14, 2006].*

* cited by examiner

*Primary Examiner*—Young J Kim
(74) *Attorney, Agent, or Firm*—Richard Aron Osman

(57) ABSTRACT

Improved methods of genetic haplotyping and DNA sequencing and mapping, including methods for making amplified ssDNA, methods for allele determination, and a DNA barcoding strategy based on direct imaging of individual DNA molecules and localization of multiple sequence motifs or polymorphic sites on a single DNA molecule.

14 Claims, 8 Drawing Sheets

Long Range PCR to generate dsDNA (>10kb) with 5' modified primers
One primers was modified at 5 ' end with biotin or a fluorophore, such as cy3.
The other primer was phosphorelated at 5 ' end.

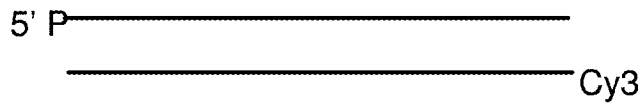

Obtain ssDNA using Lambda Exonuclease 5'-3' Cy3 or biotin streptavidin to
block the digestion of exonuclease of one strand and phosphore group at 5' end of the other
strand promote the digestion, which results in full length single stranded DNA molecules.

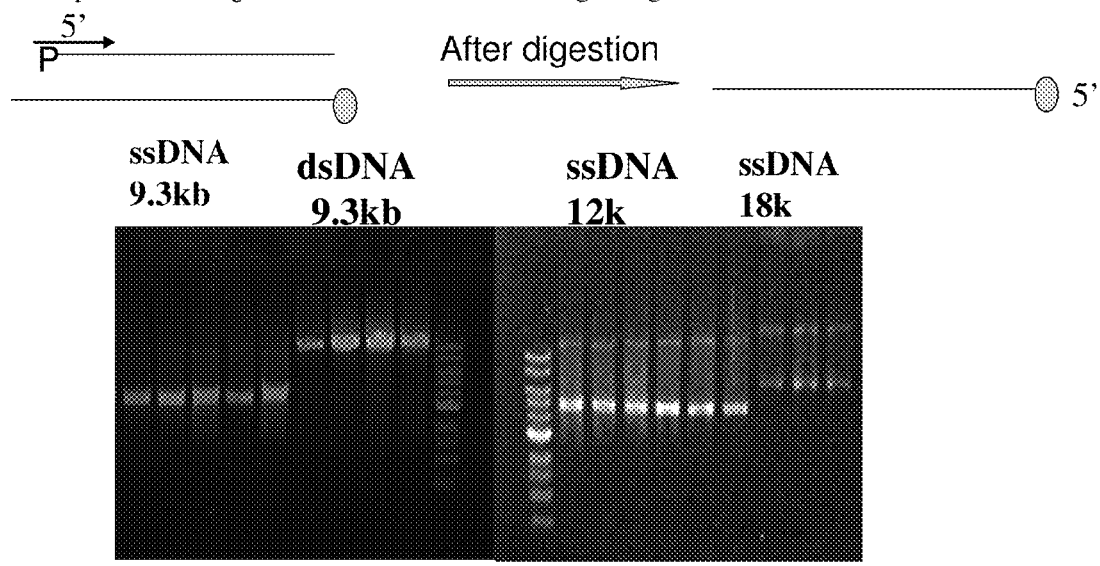

Fig. 2

Allele specific labeling of multiple SNPs simultaneously and regeneration of dsDNA for molecular haplotyping

Polymerases extent only the perfect matched the primers on the single stranded DNA templates, and at the same time, the extension converts the single stranded templates into double stranded DNA molecules.

A haplotype of 4 SNPs on12.5kb

Two haplotypes of CGTG and CAGT were determined.

Recognition sequence of nicking endonuclease Nb.BbvC I and the labeling scheme. After nicking (indicated by the arrow), a fluorescent nucleotide terminator was incorporated at the nicking site (indicated as green T) as the native T was displaced.

A.
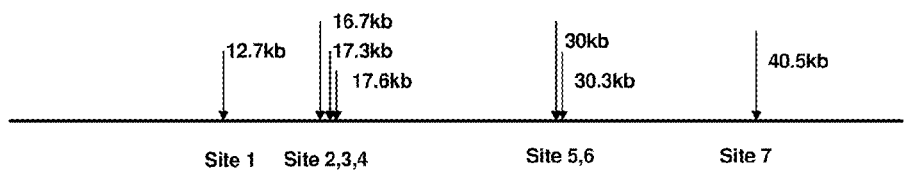
B.          48.5 kb Lambda DNA
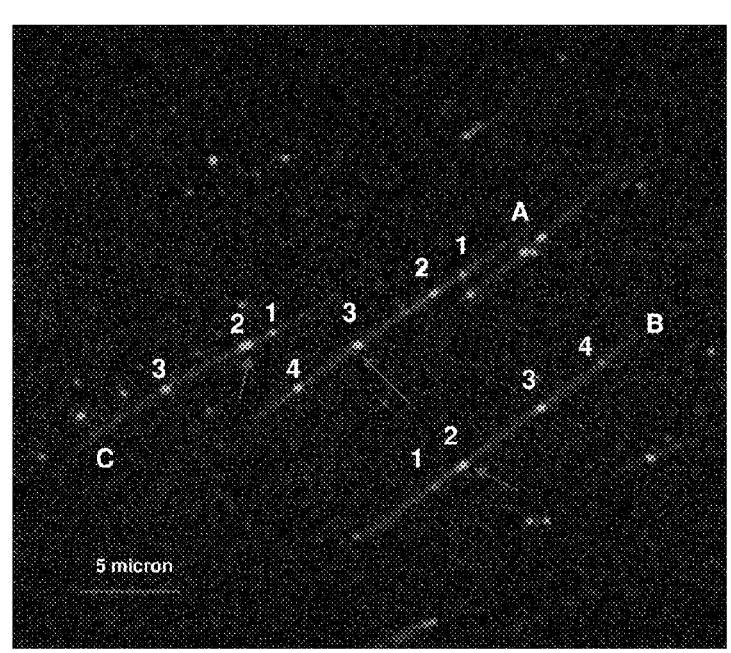
C.
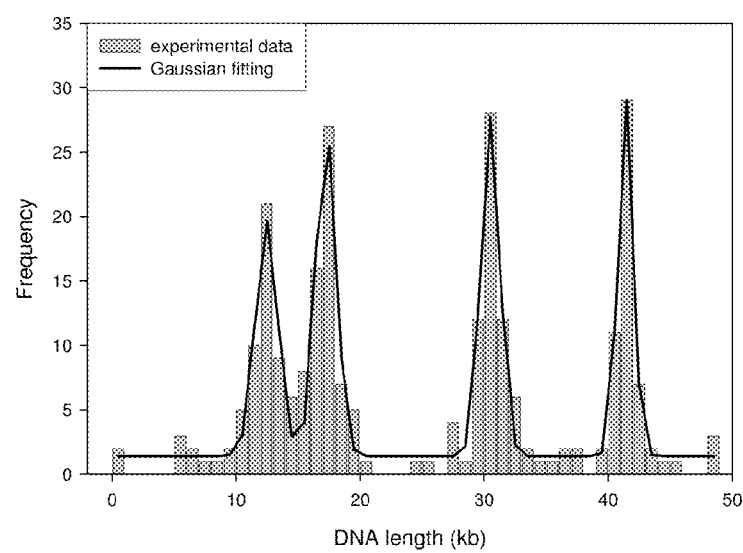
Fig. 7

METHODS FOR DETERMINING GENETIC HAPLOTYPES AND DNA MAPPING

This invention was made with US Government support under Grant Nos. PHS 5 R01-AR44420C and R01 HG001720-09 awarded by NIH. The Government has certain rights in this invention.

FIELD OF THE INVENTION

The field of the invention is determining genetic haplotypes and DNA mapping.

BACKGROUND OF THE INVENTION

The problem of genetic haplotyping of individuals and groups has existed since the study of molecular genetics began. Prior approaches of molecular haplotyping include physically separating the parental chromosomal segments followed by genotyping the isolated (and amplified) chromosomal segments, and analyzing individual DNA molecules.

DNA mapping is an important analytical tool in genomic sequence assembly, medical diagnostics, and pathogen identification. The current strategy for DNA mapping is based on sizing DNA fragments generated by enzymatic digestion of genomic DNA with restriction endonucleases. More recently, the DNA molecular combing and optical mapping techniques have been developed to interrogate multiple sequence sites on single DNA molecules deposited on a glass surface.

SUMMARY OF THE INVENTION

We have developed and disclose here methods relating to genetic haplotyping and DNA sequencing and mapping, including methods for making amplified ssDNA, methods for allele determination, and a DNA barcoding strategy based on direct imaging of individual DNA molecules and localization of multiple sequence motifs or polymorphic sites on a single DNA molecule. Compared with prior methods, our method of DNA mapping provides improved labeling efficiency, more stable labeling, high sensitivity and better resolution.

In one application, individual genomic DNA molecules or long-range PCR fragments were labeled with fluorescent dyes at specific sequence motifs or polymorphic sites. The labeled DNA molecules were then stretched into linear form on a modified glass surface and imaged using total internal reflection fluorescence (TIRF) microscopy. By determining the positions and colors of the fluorescent labels with respect to the DNA backbone, the distribution of the sequence motifs or polymorphic sites can be established with accuracy, in a manner similar to reading a barcode. This DNA barcoding method was applied in DNA optical mapping and the haplotype determination.

The disclosed methods facilitate molecular haplotyping, and encompass improved (1) methods of making ssDNA using selective digestion by lambda exonuclease; (2) methods for allele specific labeling of multiple SNPs simultaneously and regeneration of dsDNA for molecular haplotyping; (3) sequencing methods using fluorescent nucleotides and nanochannel immobilized DNA; and (4) methods for DNA mapping using a nicking endonucleases (the inventors published aspects of this last method 6 months ago: Xiao et al., Nucleic Acids Res. 2007;35(3):e16. Epub Dec. 14, 2006 Rapid DNA mapping by fluorescent single nucleotide detection). The inventions are improvements to established methods of making, labeling, and sequencing DNA, which facilitate molecular haplotyping, including the use long (10-20 Kb) templates.

Using the disclosed improvements, we have demonstrated that we can reliably and repeatably call haplotypes with multiple SNPs on long DNA fragments, and successfully construct sequence motif maps of lambda phage, a strain of human adenovirus, and several strains of human rhinoviruses. We have determined haplotypes of over 30 CEPH DNA samples ranging in size from 10-20 kb from Hapmap panel, covering over 50 kb of human chromosome 10 and 17. We have also used the disclosed improvements to obtain base-by-base sequences of the same CEPH samples.

Various embodiments of the invention are depicted in the Figures and/or otherwise described herein.

1. In one embodiment, the invention provides a method for making long (2-20 Kb) amplified ssDNA; see, for example, FIG. 2. This method comprises the steps of:

a) amplifying by long range PCR template DNA using a first primer having a 5' detectable label and a second primer having a 5' phosphore to generate amplified first strands incorporating the 5' detectable label, and amplified second strands incorporating the 5' phosphore; and b) selectively digesting the second strands with a 5'-3' exonuclease to provide long amplified, single-stranded first strands, wherein the 5' detectable label inhibits digestion of the first strand by the exonuclease.

In particular embodiments, this method provides long template ssDNA for use in other methods described and disclosed herein.

2. In another embodiment, the invention provides a method for allele specific labeling of multiple SNPs simultaneously for molecular haplotyping; see, for example FIG. 3. This embodiment involves labeling and linearizing of dsDNA, detecting SNP order, and thus provides spatial resolution. This method comprises the steps of:

a) contacting simultaneously a long (2-20 Kb) ssDNA template comprising a plurality of SNPs with a corresponding plurality of first and second allele specific primers corresponding to alternative alleles at the SNPs and comprising alternate fluorescent labels, under conditions wherein one of each of the first and second allele-specific primers hybridizes at each corresponding SNP;

b) extending simultaneously with polymerase the hybridized primers to convert the ssDNA to dsDNA comprising incorporated labels of the hybridized primers;

c) linearizing the dsDNA; and d) reading the order of the incorporated labels of the dsDNA to determine the molecular haplotype of the dsDNA.

In an alternative variation of this embodiment, the invention provides a method for allele specific labeling of multiple SNPs simultaneously for molecular haplotyping, the method comprising the steps of:

a) contacting simultaneously a long (2-20 Kb) ssDNA template comprising a plurality of SNPs with (i) a corresponding plurality of 5' flanking sequence-specific primers, and (ii) a plurality of oligos comprising 5' single nucleotides corresponding to the alternative alleles at the SNPs and corresponding fluorescent labels, under conditions wherein the primers hybridize at the corresponding 5' flanking sequences, and the oligos hybridize at the corresponding SNPs;

c) ligating the hybridized primers and abutting oligos with a ligase;

d) extending simultaneously from the ligated oligos to convert the ssDNA to dsDNA comprising incorporated labels of the ligated oligos;

e) linearizing the dsDNA; and f) detecting sequentially the incorporated labels at each SNP to infer the allele of each SNP.

In a preferred aspect of this embodiment the labeled oligos are universal, e.g. $G(N)_5$, $A(N)_5$, $C(N)_5$, and $T(N)_5$ 3. In another embodiment, the invention provides a method for allele specific labeling of multiple SNPs sequentially for allele determination; see, for example FIG. 1. In this embodiment, each SNP is interrogated individually, in time scale, one at a time, and order is determined over time scale, providing sequencing, but not single base resolution. This method comprises the steps of:

a) contacting sequentially a long (2-20 Kb) ssDNA template comprising a plurality of SNPs and corresponding 5' flanking sequences, with a corresponding plurality of 5' flanking sequence-specific primers, under conditions wherein the primers hybridize at the corresponding 5' flanking sequences;

b) extending sequentially the 3' end of the hybridized primers single nucleotides corresponding to the alternative alleles at the SNP and comprising corresponding fluorescent labels, wherein the nucleotides are added by single-base primer extension or oligo ligation; and c) detecting sequentially the incorporated labels at each SNP to infer the allele of each SNP.

In this embodiment, the contacting-extending-detecting steps are practiced sequentially, such that the three-step process is repeated for each SNP. This embodiment can be practiced with either primer extension, or by oligo addition with ligase.

4. In another embodiment, the invention provides a method for sequencing a long (2-20 Kb) ssDNA; see, for example FIG. 1. This embodiment is used for sequencing, and comprises the steps of:

a) hybridizing one or more primers to a long template ssDNA confined in two-dimensions in a channel or on a solid surface;

b) adding to the 3' end of the hybridized primers fluorescently-labeled nucleotides by polymerase extension or fluorescently-labeled oligos by ligase ligation, to obtain fluorescently-labeled dsDNA; and c) sequentially reading each of the incorporated fluorescently-labeled nucleotides or fluorescently-labeled oligo sequence of the dsDNA using TIRF microscopy to obtain a base-by-base sequence of the dsDNA.

In particular versions of this embodiment, the recited primer is one of multiple primers. The support on/in which the ssDNA is confined may be a solid surface, wherein the ssDNA is not linearized, a channel, which may be a micro- or nano-channel (100-200 nm dia), wherein the ssDNA is stretched for distance resolution, etc. Critical is that the ssDNA be confined in the two-dimensional discernable plane of the TIRF, up to about 100-200 nm. The primer ligation embodiment may be implemented by ligating $G(N)_5$ (or $A(N)_5$, or $C(N)_5$, or $T(N)_5$) oligos, each time the SNP base is interrogated. In a particular embodiment, the long template ssDNA is produced by the method depicted in FIG. 2.

5. In another embodiment, the invention provides a method of DNA mapping; see, for example FIG. 7. This embodiment is applicable to genomic DNA, and comprises the steps of:

a) nicking one strand of a long (>2 Kb) double stranded genomic DNA molecule with a nicking endonuclease to introduce nicks at specific sequence motifs;

b) incorporating fluorescent dye-labeled nucleotides at the nicks with a DNA polymerase;

c) staining the backbone of the genomic DNA;

d) stretching the labeled DNA molecule into linear form on a modified glass surface; and e) determining the positions of the fluorescent labels with respect to the DNA backbone using total internal reflection fluorescence (TIRF) microscopy to obtain a map or barcode of the DNA.

The recited staining step is typically practices with a dsDNA intercalating dye such as YoYo (this step may be practiced before or after the stretching step). This embodiment of the invention has several applications, including pathogen identification, sequence assembly, haplotyping, etc.

The individual steps or laboratory techniques embodied in our methods are generally known and well-described in the art, and not belabored here. These include DNA sequencing, stretching, polymerization, ligation, digestion, labeling, staining, PCR, etc. For example, applicable techniques include molecular combing (e.g. Science. Sep. 30, 1994; 265, 2096-8; U.S. Pat. No. 5,840,862), optical mapping (e.g. U.S. Pat. No. 6,174,671), single molecule localization (e.g. Schmidt, T., Schutz, et al., 1996, Proc. Natl. Acad. Sci. USA 93, 2926-2929; Thompson, et al., 2002, Biophys J 82, 2775-83; Yildiz, et al., 2003, Science 300, 2061-2065) related genotyping methods (e.g. Proc. Natl. Acad. Sci. USA 95, 8046-8051, Jul. 7, 1998; Nat Biotechnol. 18:760-763). Similarly, the individually-recited materials and reagents, such as substrates and channels suitable for attaching and stretching DNA, labels, fluorescent labels, phosphores, oligos, polymerase, ligase, exonuclease, etc. are all generally known and well-described in the art, and not belabored here.

BRIEF DESCRIPTION OF THE FIGURES

FIG. 2 depicts the method of generating long single stranded DNA molecules.

FIG. 7A-C depict the sequence motif map of lambda phage DNA; (A) the predicted nicking sites of lambda DNA; (B) overlapped 2 colored image of lambda DNA; (C) the sequence motif map obtained by single molecule DNA barcoding.

DETAILED DESCRIPTION OF SPECIFIC EMBODIMENTS OF THE INVENTION

Long range PCR is a mature technique, with robust protocols and highly efficient enzymes commercially available for this purpose (Barnes, 1994, Proc Natl Acad Sci USA 91(6): 2216-2220; Cheng, et al., 1994, Proc Natl Acad Sci USA 91(12):5695-5699). We have developed a protocol wherein after obtaining long double stranded DNA molecules, one of the strands is protected from lambda exonuclease digestion with chemical groups at 5' end, while the other unprotected strand is completely digested by lambda exonuclease (FIG. 2). Using this protocol, single stranded DNA molecules from 2 kb to 20 kb can be obtained (FIG. 2).

Figure 1:
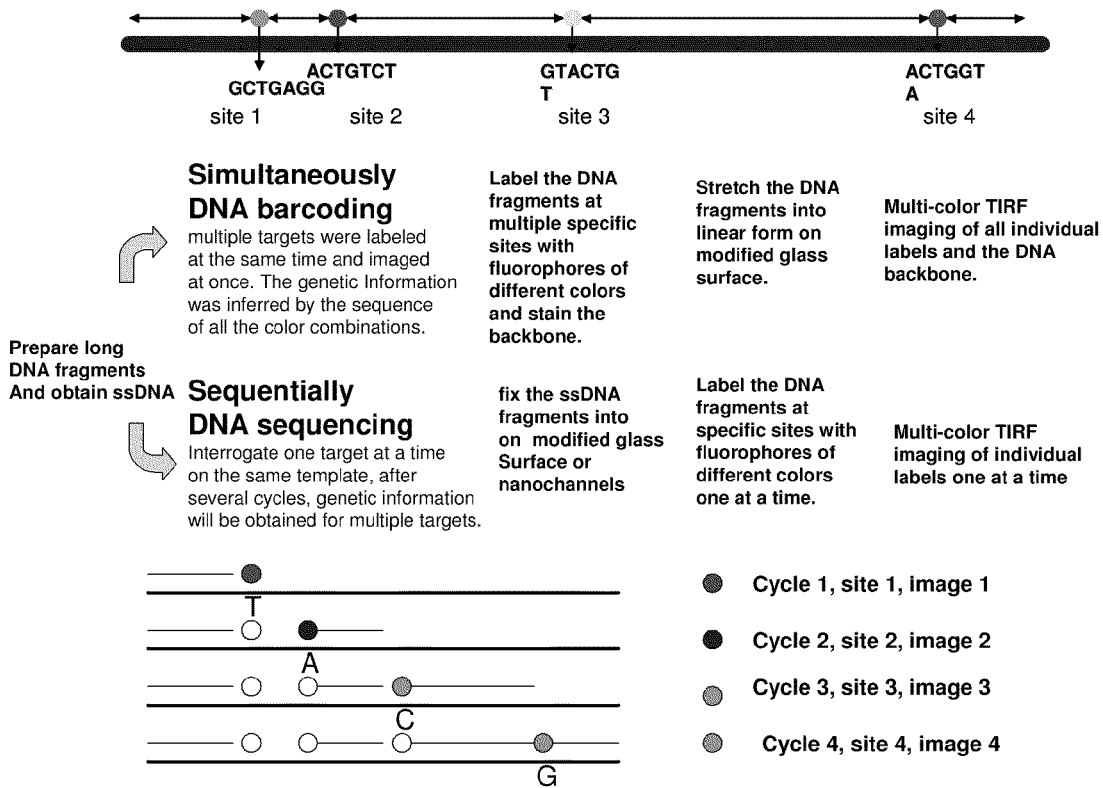
FIG. 1 depicts simultaneous and sequential single molecule DNA barcoding.
Figure 3:
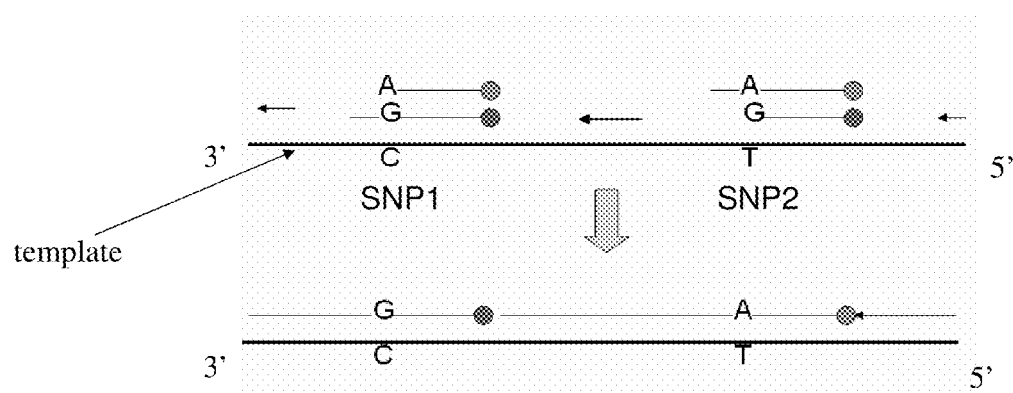
FIG. 3 deptics allele specific labeling of multiple SNPs for simultaneous haplotype determination.
Figure 4:
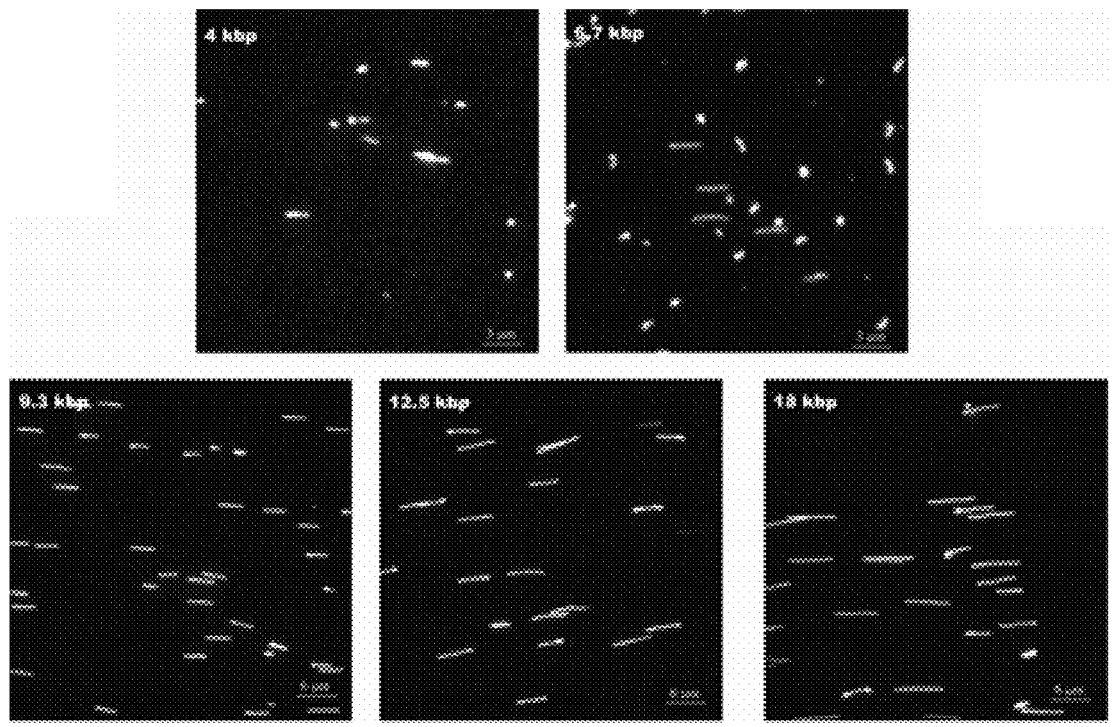
FIG. 4 depicts linearizing DNA molecules on modified glass coverslips.
Figure 5:
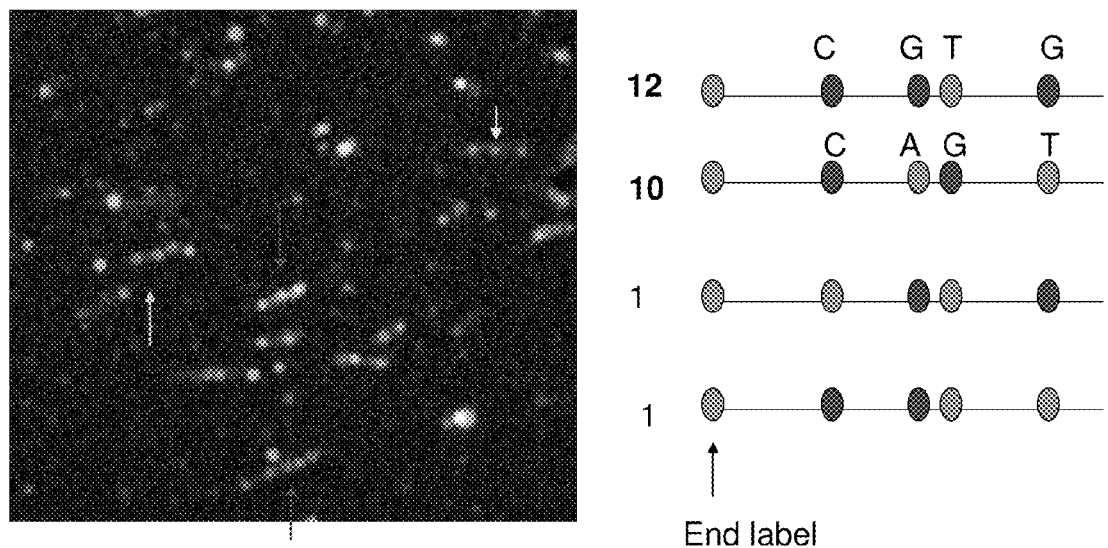
FIG. 5 depicts haplotyping results from simultaneous haplotype determination.

A number of methods are available for labeling DNA, and all of them involve a hybridization step. We developed an allele-specific primer extension method for DNA haplotyping and RNA splicing. This strategy requires only a simple step that is accomplished in a closed tube experiment (FIG. 3). A fluorescent dye labeled primer is designed to contain DNA sequences complementary to target sequences. Only probes with perfect match can be extended and stay on the DNA backbone. Based on the DNA sequence surrounding the multiple target sequences, probes can be designed to hybridize under the same, standard conditions. The primers can then hybridize to the target sequences and be extended on the template simultaneously or sequentially. In the case of the simultaneous labeling scheme, multiple primers were extended at multiple target sequences and a double stranded DNA molecule was regenerated with all the labels on the backbone. After labeling, DNA is mounted on a glass coverslip coated with charged polymers. The DNA is drawn between the coverslip and a glass slide by capillary action. One end of the DNA molecules binds to the charged surface, and the strong directional flow due to the capillary action causes the DNA fragments to be stretched and aligned along the direction of flow (FIG. 4). The DNA fragments can then be imaged, and the sequences of the dye molecules on the backbone determined, e.g. FIG. 5.

In the case of the sequential scheme, the DNA molecules are first fixed on the surface or in the nanochannels. Each base or allele was labeled and imaged independently on the same template. The genetic information was then inferred in a manner of the sequential appearances of the fluorophores along the time scale.

DNA mapping is an important analytical tool in genomic sequence assembly, medical diagnostics, and pathogen identification. The current strategy for DNA mapping is based on sizing DNA fragments generated by enzymatic digestion of genomic DNA with restriction endonucleases. This approach not only needs large quantity of DNA materials, it also loses the order of the DNA fragments.

Figure 6:
FIG. 6 depicts recognition sequence of nicking endonuclease Nb.BbvC I and the nick-labeling scheme.

An improvement provided here starts with introducing nicks in double-stranded DNA at specific sequence motifs recognized by nicking endonucleases, which cleave only one strand of a double-stranded DNA substrate. Fluorescent dye terminators are then incorporated at these sites by DNA polymerase (FIG. 6). The labeled DNA molecules are stretched into linear form on a modified glass surface and individually imaged using multicolor total internal reflection fluorescence (TIRF) microscopy, a technique capable of localizing single fluorescent dye molecules with nanometer-scale accuracy. By determining the positions of the fluorescent labels along the DNA backbone, the distribution of the sequence motifs recognized by the nicking endonuclease can be established with great accuracy, in a manner similar to reading a barcode. With this approach, we constructed sequence motif maps of lambda phage, a strain of human adenovirus, and several strains of human rhinoviruses.

FIG. 7 show the sequence motif map of lambda DNA: A. The predicted Nb.BbvC I map of lambda DNA. Positions of the nicking sites are indicated by arrows. Nicking sites 2-4 and 5-6 are closely clustered and are not resolvable due to the limits of optical diffraction. B. In the intensity scaled composite image of linear lambda DNA, the Nb.BbvC I sites (labeled with Tamra-ddUTP) are shown as green spots and the DNA backbone (labeled with YOYO) is shown as blue lines. Due to the diffraction limits of the microscope, only 4 labels can be fully resolved. In this field, two DNA fragments (A and B) are fully labeled while one fragment (C) has 3 labels. Red arrows point to clustered sites, some of them are brighter than other because of the presence of multiple labels. C. The sequence motif map in the bottom graph was obtained by analyzing 61 single molecule fluorescence images. The solid line is the Gaussian curve fitting and the peaks correspond well to the predicted locations of the sequence motif. The inset shows the labeling efficiency, 81 DNA molecules out of a total 112 DNA molecules have more than 3 labels.

Figure 8:
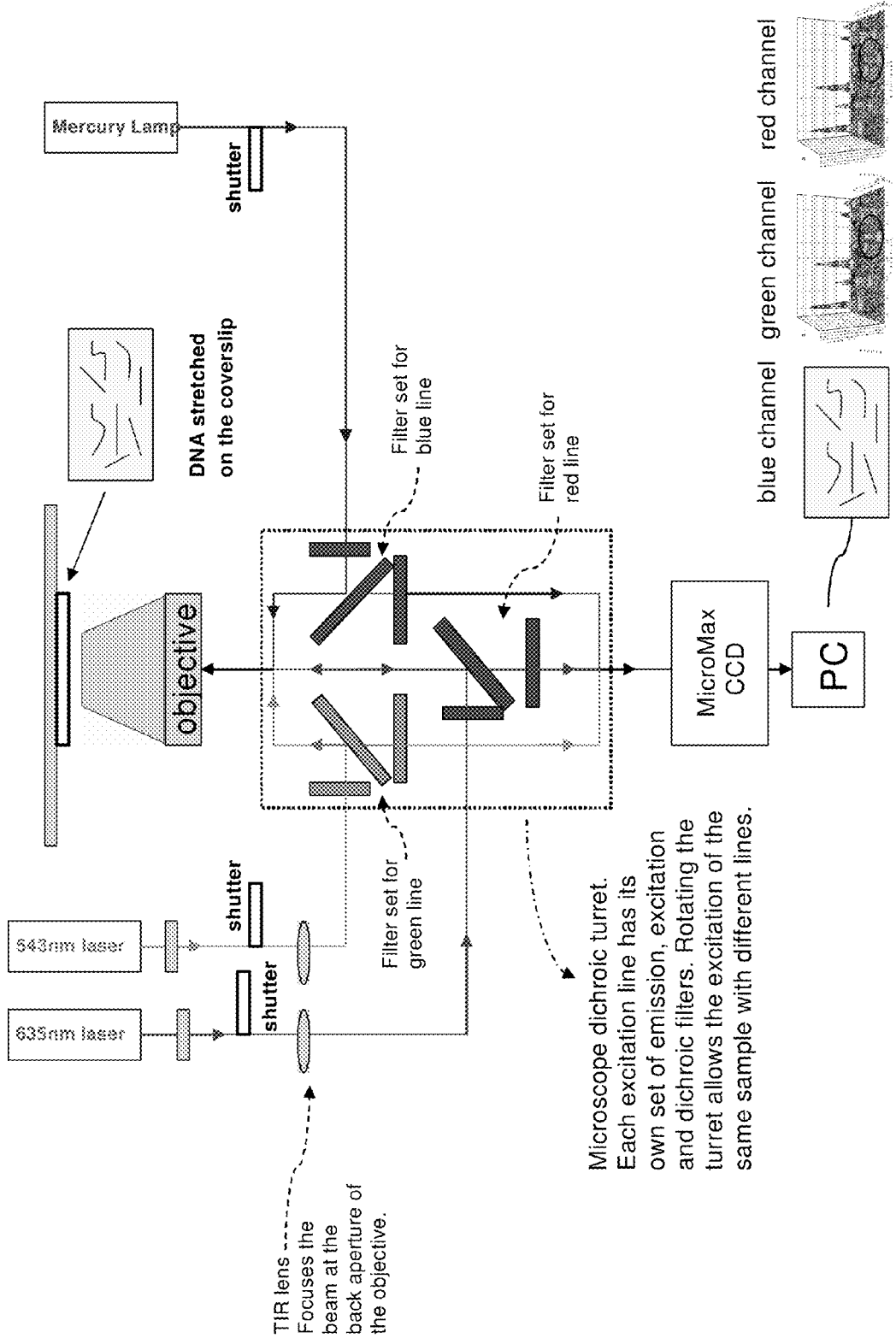
FIG. 8 depicts a TIRF imaging system for high resolution single fluorophore imaging.

The imaging technique we adopted in these examples is based on an extension of FIONA (Fluorescence Imaging with One Nanometer Accuracy) (Yildiz, et al., 2003, Science 300 (5628):2061-2065.; Yildiz, et al., 2004, Science 303(5658): 676-678) See FIG. 5. SNPs found in 10-20 kb long PCR fragments are labeled in an allele specific fashion by incorporating nucleotides bearing fluorescent dyes (such as Cy-3 and Cy-5) whereas the DNA backbone is stained with blue color dye YOYO-1 (or POPO-1). Total internal reflection epi-fluorescence microscopy (TIRM) (Axelrod, 1989, Meth Cell Biol 30:245-270.; Tokunaga, et al., 1997, Biochem Biophys Res Comm 235(1):47-53.), is used to excite and image the individual fluorophores attached to the DNA backbone using a slow-scan back-thinned CCD camera (FIG. 8). The localization of single fluorescent molecule is done by centroid analysis (Thompson, et al., 2002, Biophys J 82(5):2775-2783.).

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of DNA mapping, the method comprising the steps of:
    a) nicking one strand of a long (>2Kb) double stranded genomic DNA molecule with a nicking endonuclease to introduce nicks at specific sequence motifs;
    b) incorporating fluorescent dye-labeled nucleotides at the nicks with a DNA polymerase, under conditions wherein only a single nucleotide is incorporated at each of the nicks;
    c) staining the backbone of the genomic DNA;
    d) stretching the labeled DNA molecule into linear form on a modified glass surface; and
    e) determining the positions of the fluorescent labels with respect to the DNA backbone using total internal reflection fluorescence (TIRF) microscopy to obtain a map or barcode of the DNA.

2. The method of claim 1, wherein the determining step comprises individually localizing the fluorescent dye labels with nanometer-scale accuracy.

3. The method of claim 1, wherein total internal reflection epi-fluorescence microscopy (TIRM) is used to excite and image individual fluorophores of the labels attached to the DNA backbone using a slowscan back-thinned CCD camera.

4. The method of claim 1, wherein localization of individual fluorophores of the labels is done by centroid analysis.

5. The method of claim 1, wherein the determining step comprises individually localizing the fluorescent dye labels with nanometer-scale accuracy,
    wherein total internal reflection epi-fluorescence microscopy (TIRM) is used to excite and image individual fluorophores of the labels attached to the DNA backbone using a slowscan back-thinned CCD camera, and wherein localization of the individual fluorophores is done by centroid analysis.

6. The method of claim 5, wherein the endonuclease is Nb.BbvC I.

7. The method of claim 5, wherein one of the fluorescent dye-labeled nucleotides is Tamra-ddUTP.

8. The method of claim 1, wherein the incorporating and determining steps are repeated in multiple cycling reactions with different nucleotides to determine multiple bases downstream (5' to 3') of the nicks.

9. A method of DNA mapping, the method comprising the steps of:
   a) nicking one strand of a long (>2Kb) double stranded genomic DNA molecule with a nicking endonuclease to introduce nicks at specific sequence motifs;
   b) incorporating fluorescent dye-labeled nucleotides at the nicks with a DNA polymerase, under conditions wherein only a single nucleotide is incorporated at each of the nicks;
   c) staining the backbone of the genomic DNA;
   d) stretching the labeled DNA molecule into linear form on a modified glass surface; and
   e) determining the positions of the fluorescent labels with respect to the DNA backbone using total internal reflection fluorescence (TIRF) microscopy to obtain a map or barcode of the DNA,
   wherein in the incorporating step (b), the nucleotides A, T, G and C, each with a different fluorescent label are incorporated; and in the determining step (e), the positions of each of the labels are determined simultaneously.

10. The method of claim 9, wherein the determining step comprises individually localizing the fluorescent dye labels with nanometer-scale accuracy.

11. The method of claim 9, wherein total internal reflection epi-fluorescence microscopy (TIRM) is used to excite and image individual fluorophores of the labels attached to the DNA backbone using a slowscan back-thinned CCD camera.

12. The method of claim 9, wherein localization of individual fluorophores of the labels is done by centroid analysis.

13. The method of claim 9, wherein the determining step comprises individually localizing the fluorescent dye labels with nanometer-scale accuracy,
   wherein total internal reflection epi-fluorescence microscopy (TIRM) is used to excite and image individual fluorophores of the labels attached to the DNA backbone using a slowscan back-thinned CCD camera, and
   wherein localization of the individual fluorophores is done by centroid analysis.

14. The method of claim 13, wherein one of the fluorescent dye-labeled nucleotides is Tamra-ddUTP.

* * * * *